United States Patent [19]

Winchel

[11] Patent Number: Plant 5,608

[45] Date of Patent: Dec. 24, 1985

[54] ROSE PLANT—DOLLY PARTON VARIETY

[75] Inventor: Joseph F. Winchel, Harbor City, Calif.

[73] Assignee: The Conard-Pyle Company, West Grove, Pa.

[21] Appl. No.: 579,980

[22] Filed: Feb. 14, 1984

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which continually bears very large attractive fully double rich orange-red blossoms on strong sturdy stems. Such robust blossoms further can be characterized by their distinctive outstanding fragrance which is heady and somewhat fruity in nature. Accordingly, the present variety can be relied upon to give a colorful and fragrant garden display from spring to the first frost of fall. The new variety resulted from the crossing of the Fragrant Cloud variety (U.S. Plant Pat. No. 2,574) and the Oklahoma variety (U.S. Plant Pat. No. 2,326).

1 Drawing Figure

SUMMARY OF THE INVENTION

The new and distinct variety of Hybrid Tea rose plant of the present invention was created by artificial pollination wherein two parents were crossed which previously had been studied for the possible possession of the characteristics sought in the new variety. The parents of the new variety were the Fragrant Cloud variety (U.S. Plant Pat. No. 2,574) and the Oklahoma variety (U.S. Plant Pat. No. 2,326).

Seeds from the artificial pollination were sown, and the resulting seedlings were observed. Selective study resulted in the identification of a single plant of the new variety. The desirable qualities of the new variety have been confirmed through extensive testing and the importance of the new variety has been firmly established.

It was found that the new variety of Hybrid Tea rose plant of the present invention possesses the following characteristics:

(a) forms attractive very large fully double blossoms of orange-red coloration, (b) exhibits an outstanding blossom fragrance, (c) exhibits excellent blossom form, (d) forms strong sturdy stems, (e) exhibits exceptional vigor which creates a well-branched broad and upright plant, and (f) exhibits above average disease resistance.

The orange-red blossoms are generally without blemish or streaking. Only under the hot summer sun do the outer edges of the petals show any color change as they take on a rich red shade. As the blossoms open, the outer petals gently roll back while the inner petals tend to hold to give a high-centered bloom that almost always hides the center. Eventually the petals will open out to form an attractive cup-shaped very double flower. The new variety tends to blossom continually and can be considered to be ever-blooming. The fragrance of the blossoms is exceptional and is exhibited from the time the first petal unfurls until the last petal drops. Such fragrance is heady and somewhat fruity in nature.

In view of these characteristics the new variety meets the needs of the horticultural industry for all purposes, and is particularly well suited for growing by the home gardener as a flowering shrub whose well-formed, highly fragrant blossoms are ideal for cutting and exhibiting.

The new variety has been found to readily undergo propagation by budding and by cuttings. The characteristics of the new variety have been found to be strictly transmissible by such asexual propagation.

The new variety has been named the DOLLY PARTON variety.

BRIEF DESCRIPTION OF PHOTOGRAPH

The accompanying photograph shows as nearly true as it is possible to make the same in a color illustration of this character, typical specimens of plant parts obtained from plants of the new variety grown in the field at West Grove, Pa.

In the upper left portion of the photograph young foliage is shown. At the upper right a segment of a strong sturdy stem which is typical of the new variety is shown. At the upper left center of the photograph buds of the new variety in two stages of opening are shown. Across the left and center of the photograph three attractive very large fully double blossoms of the new variety are shown in various stages of opening.

DETAILED DESCRIPTION

The chart used in the identification of the colors is that of The Royal Horticultural Society (R.H.S. Colour Chart). The plants described were budded on *Rosa frobeli* rootstock, and were three years old. They were grown in the field at West Grove, Pa.

Class: Hybrid Tea.

Plant: Upright, broad and medium high bush.

Branches:

*Color.*—Young stems: Predominantly Yellow-Green Group 144A with red tones of Red-Purple Group 60B on side exposed to the sun. Mature stems: Predominantly Yellow-Green Group 144A with red tones of Red-Purple Group 60B on side exposed to the sun.

*Thorns.*—Shape: Upper edge: Convex. Under edge: Concave. Base: Elliptical. Quantity: Many. Color: On young stems: Red-Purple Group 60C with a few areas of Yellow-Green Group 144C scattered over thorn surface. On mature stems:

Red-Purple Group 60A at the thorn base blending to Yellow-Green Group 144B at the tip.

Leaves:

*Petioles.*—Inner surface: Generally Yellow-Green Group 144C, however, some petioles show tones of Red-Purple Group 60B. Outer surface: Generally between Yellow-Green Group 144C and 144D, however, some petioles show tones of Red-Purple Group 60B.

*Thorns.*—Number: Approximately two to five prominent thorns with an average of approximately three. Color: Generally Yellow-Green Group 144D, however, some thorns have a tinge of Red-Purple Group 60C.

*Leaflets.*—Number: Generally three to five leaflets per leaf. Shape: Ovate to elliptical with a rounded or sometimes oblique base, the leaflet tip is acute to obtuse, the margins are serrulate. Size: Approximately 2 to 7 cm. in length (approximately 5.5 cm. in length on average), and approximately 1 to 5 cm. in width (approximately 3.5 cm. in width on average). General effect: Slightly glossy.

*Leaves.*—Size: Approximately 7 to 15 cm. in length (approximately 12 cm. in length on average). Color: Young foliage: Upper surface: Green Group 138C with red tones over the entire leaf surface of Red-Purple Group 60B. Lower surface: Red-Purple Group 60B with tones of Green Group 138B. Color: Mature foliage: Upper surface: Green Group 137A. Lower surface: Green Group 138C with tones of Red-Purple Group 60A.

Inflorescence:

*Number of flowers.*—Generally the blossoms are borne singly, however, sometimes blossom clusters are formed which range in number from 2 to 5 blossoms per cluster (approximately 2 on average).

*Peduncle.*—Color when young: Yellow-Green Group 144A. Color when mature: Yellow-Green Group 144B with tones of Red Group 53D.

*Bud.*—Shape when closed: Rounded at base and pointed at tip. Shape when opening: Rounded at base and pointed at tip. Length: Large, usually more than two inches. Color: When opening:

Upper surface: Red Group 40D which blends with Red-Purple Group 60A toward the center of the base. The outer petals have a center streak of White Group 155A. Under surface: Red-Purple Group 60A with occasional tips of Black Group 202A.

*Flower.*—Form: Very double flower, generally 35 or more petals, as the flower first opens the center is raised with many petals overlapping, eventually the petals sufficiently open to form a cup-shaped flower. Diameter: Approximately 9 to 15 cm. (approximately 11 cm. on average). Color: When partially open: Upper surface: Red-Orange Group 40B blending at the edges to Red Group 53C. There is a ring of color at the petal base of Red Group 53B and the basal tip is Yellow Group 12A. Under surface: Red Group 53C darkening to Red Group 53A at the petal base. Color: When fully open: Upper surface: Red Group 40B blending at the edges to Red Group 53C. There is a ring of color at the petal base of Red Group 53B and the basal tip is Yellow Group 12A. Under surface: Red Group 53C darkening to Red Group 53A at the petal base. Color: When fully open: Upper surface: Red Group 40B blending at the edges to Red Group 53C. There is a ring of color at the petal base of Red Group 53B and the basal tip is Yellow Group 12A. Under surface: Between Red Group 53C and Red Group 53D. Fragrance: Extremely fragrant. Lasting quality: average.

Development:

*Vegetation.*—Vigorous.

*Blossoming.*—Continuous and average.

*Resistance to disease.*—Above average.

I claim:

1. A new and distinct variety of Hybrid Tea rose plant, substantially as herein shown and described, characterized particularly by (a) attractive very large fully double blossoms of orange-red coloration, (b) outstanding blossom fragrance, (c) excellent blossom form, (d) strong sturdy stems, (e) exceptional vigor which forms a well-branched broad and upright plant, and (f) above average disease resistance.

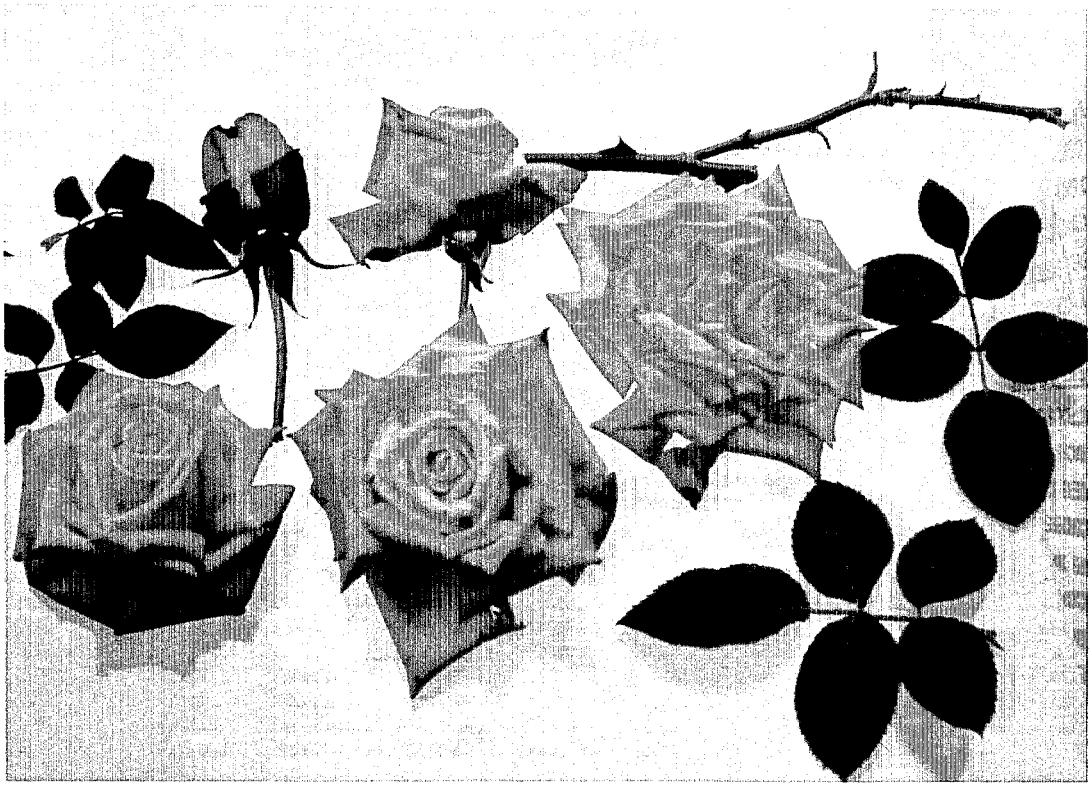

* * * * *